United States Patent
Schmidt et al.

(10) Patent No.: US 11,207,452 B2
(45) Date of Patent: Dec. 28, 2021

(54) MULTI-LUMEN TUBE ASSEMBLIES FOR MEDICAL FLUID PUMPING SYSTEMS

(71) Applicant: Fresenius Medical Care Holdings, Inc., Waltham, MA (US)

(72) Inventors: Daniel Schmidt, Petaluma, CA (US); Bert D. Egley, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 154 days.

(21) Appl. No.: 16/556,428

(22) Filed: Aug. 30, 2019

(65) Prior Publication Data

US 2021/0060227 A1    Mar. 4, 2021

(51) Int. Cl.
*A61M 1/16* (2006.01)
*A61M 1/28* (2006.01)
*A61M 1/26* (2006.01)

(52) U.S. Cl.
CPC .......... *A61M 1/1621* (2014.02); *A61M 1/287* (2013.01); *A61M 1/267* (2014.02); *A61M 2205/12* (2013.01)

(58) Field of Classification Search
CPC .... A61M 1/1621; A61M 1/287; A61M 1/267; A61M 2205/12; A61M 39/12; A61M 2039/082; A61M 2039/1066; A61M 39/105; A61M 1/14; A61M 1/285
See application file for complete search history.

(56) References Cited

U.S. PATENT DOCUMENTS

| | | |
|---|---|---|
| 4,950,245 A | 8/1990 | Brown et al. |
| 7,935,074 B2 | 5/2011 | Plahey et al. |
| 8,192,401 B2 | 6/2012 | Morris et al. |
| 8,740,959 B2 | 6/2014 | Machold et al. |
| 9,180,240 B2 | 11/2015 | Farrell et al. |
| 9,186,449 B2 | 11/2015 | Singh et al. |
| 9,500,188 B2 | 11/2016 | Ly et al. |
| 9,610,392 B2 | 4/2017 | Farrell et al. |
| 2005/0267445 A1* | 12/2005 | Mendels ............... A61M 39/10 604/534 |
| 2006/0186061 A1* | 8/2006 | Briggs ................ A61M 1/0227 210/787 |
| 2006/0195064 A1 | 8/2006 | Plahey et al. |
| 2006/0222561 A1* | 10/2006 | Hutchinson ......... F04B 43/1292 422/44 |

(Continued)

FOREIGN PATENT DOCUMENTS

| | | | |
|---|---|---|---|
| EP | 3421062 A2 * | 1/2019 | ............. B32B 27/22 |
| WO | WO 94/20155 | 9/1994 | |

(Continued)

OTHER PUBLICATIONS

PCT International Search Report and Written Opinion in International Appln. No. PCT/US2020/047634, dated Nov. 20, 2020, 15 pages.

*Primary Examiner* — Krishnan S Menon
(74) *Attorney, Agent, or Firm* — Fish & Richardson P.C.

(57) ABSTRACT

An assembly comprises a manifold configured to couple to a medical fluid cassette and a multi-lumen tube comprising a plurality of lumens within an outer wall of the multi-lumen tube. The manifold has a plurality of fluid connection ports and can be connected to the multi-lumen tube (e.g., via an adapter).

20 Claims, 8 Drawing Sheets

(56) References Cited

U.S. PATENT DOCUMENTS

| | | | |
|---|---|---|---|
| 2009/0224529 A1* | 9/2009 | Gill | A61M 39/105 |
| | | | 285/23 |
| 2011/0015610 A1 | 1/2011 | Plahey et al. | |
| 2012/0230844 A1 | 9/2012 | Farrell et al. | |
| 2012/0271226 A1 | 10/2012 | Farrell et al. | |
| 2013/0104884 A1* | 5/2013 | Vazales | A61M 16/0427 |
| | | | 128/202.16 |
| 2013/0304039 A1* | 11/2013 | Chung | A61M 39/105 |
| | | | 604/537 |
| 2019/0143093 A1* | 5/2019 | Zumbrum | A61M 39/08 |
| | | | 138/99 |
| 2020/0086018 A1* | 3/2020 | Jardret | A61M 39/1011 |

FOREIGN PATENT DOCUMENTS

| WO | WO 2004/009158 | 1/2004 |
| WO | WO 2005/014139 | 2/2005 |
| WO | WO 2012/087798 | 6/2012 |
| WO | WO2019174690 A1 * | 9/2019 |

\* cited by examiner

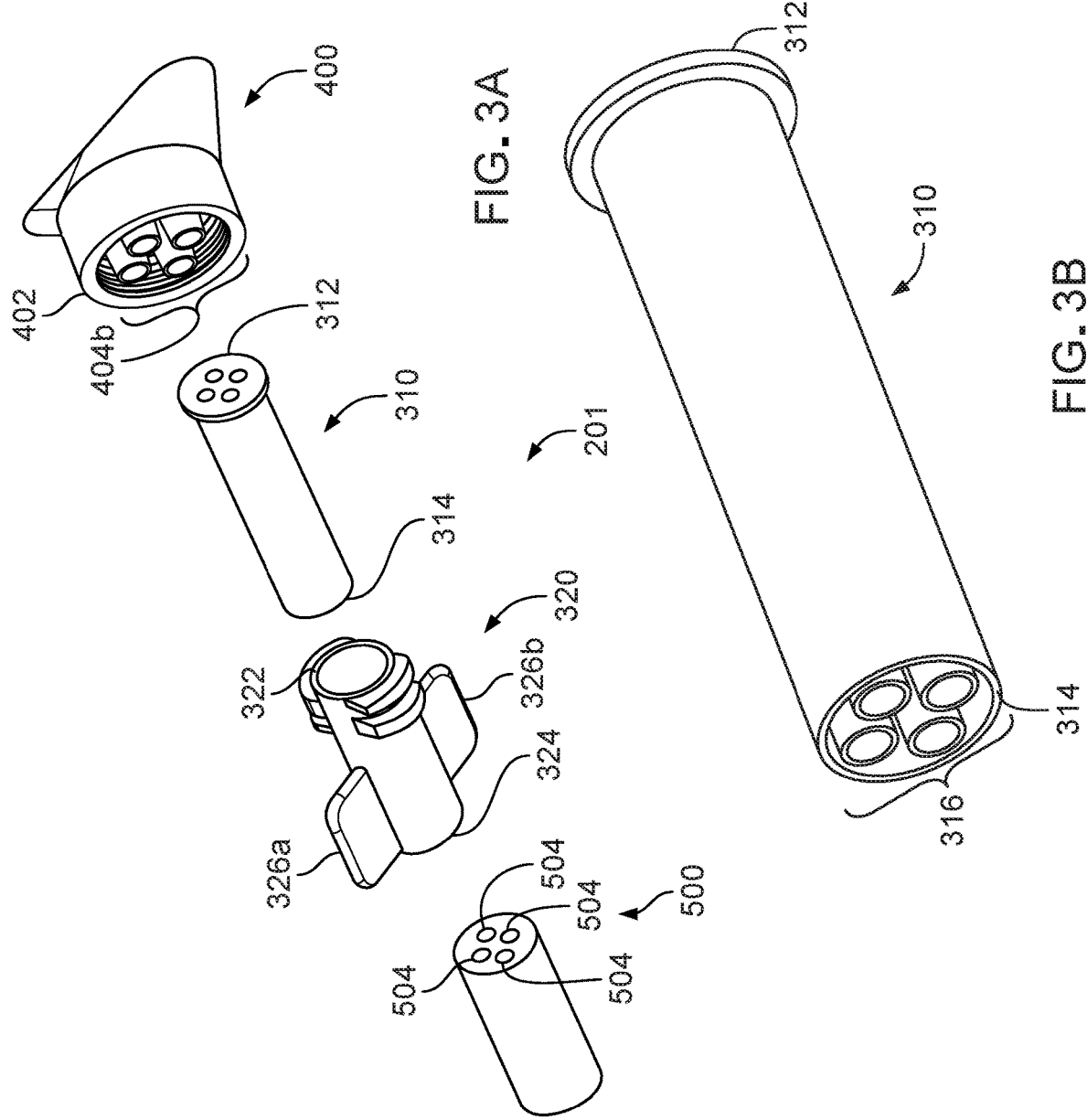

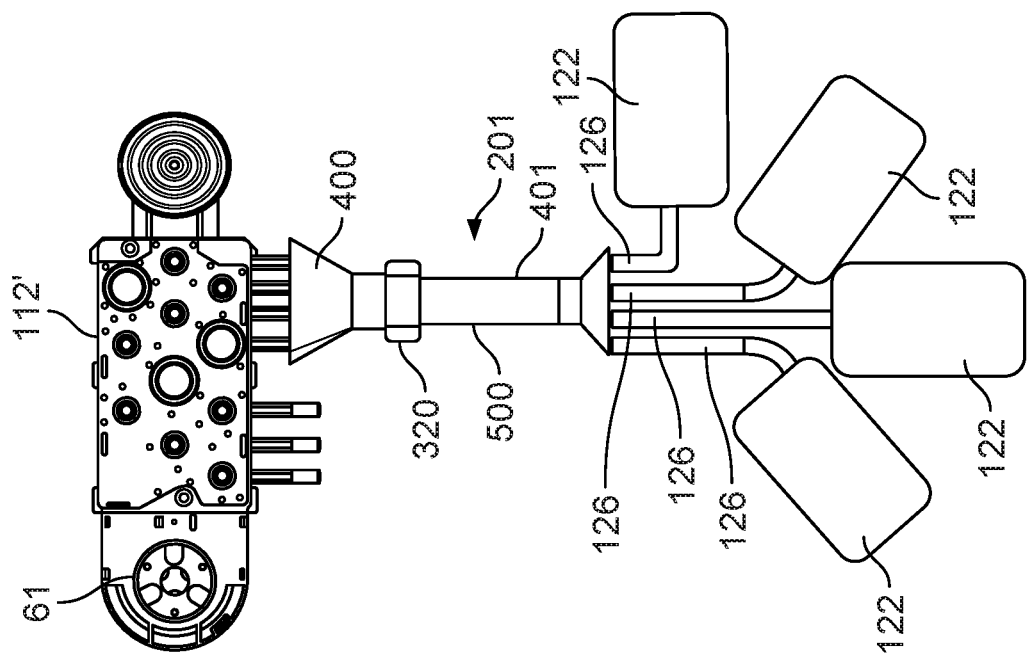
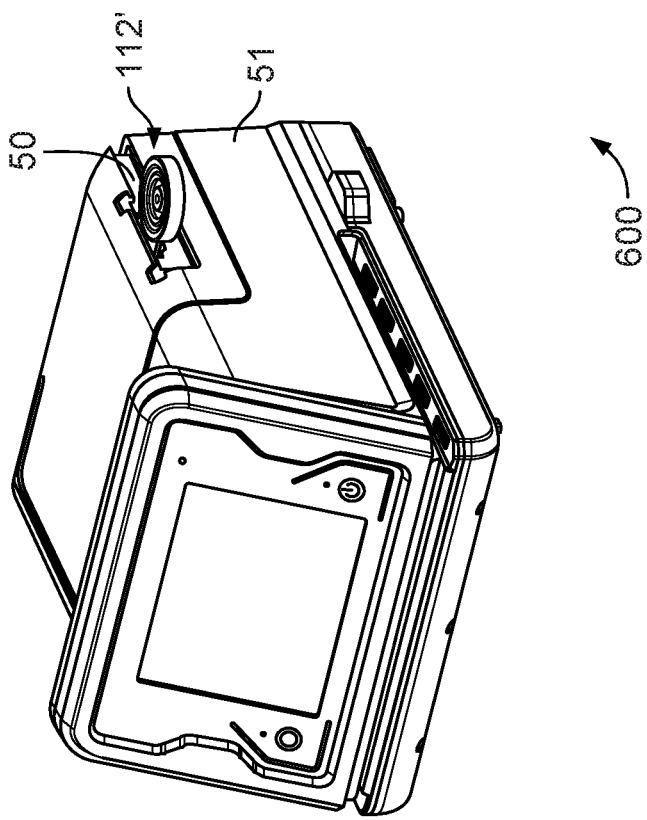
FIG. 6A

MULTI-LUMEN TUBE ASSEMBLIES FOR MEDICAL FLUID PUMPING SYSTEMS

TECHNICAL FIELD

This disclosure relates to multi-lumen tube assemblies for medical fluid pumping systems.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

SUMMARY

In one aspect, an assembly comprises a manifold configured to couple to a medical fluid cassette and a multi-lumen tube comprising a plurality of lumens within an outer wall of the multi-lumen tube. The manifold has a plurality of fluid connection ports and can be connected to the multi-lumen tube (e.g., via an adapter).

In another aspect, an assembly comprises a manifold, a multi-lumen tube, an adapter, and a threaded connector. The manifold comprises a thread portion and multiple fluid connection ports. The manifold is configured to couple to a medical fluid cassette. The multi-lumen tube comprises multiple lumens within an outer wall of the multi-lumen tube. The adapter comprises a first end and a second end opposite the first end. The first end is configured to mate with the manifold. The second end is configured to mate with the multi-lumen tube. The adapter defines multiple passages between the first and second ends. Each passage connects one of the fluid connection ports of the manifold to a corresponding lumen of the multi-lumen tube when the adapter is mated with the manifold and the multi-lumen tube. The threaded connector comprises a first end and a second end opposite the first end. The threaded connector defines an inner bore between the first and second ends of the threaded connector. The inner bore of the threaded connector is configured to receive the adapter. The threaded connector is rotatable relative to the adapter. The first end of the threaded connector is threaded and configured to mate with the threaded portion of the manifold to secure the adapter to the manifold.

In another aspect, a medical fluid cassette comprises a body and a manifold connected to the body. The body at least partially defines multiple fluid passages. The body comprises multiple fluid line connectors in fluid communication with the fluid passages. The manifold comprises multiple fluid connection ports. The manifold is configured to mate with a multi-lumen tube comprising multiple lumens disposed within an outer wall of the multi-lumen tube. Each fluid connection port mates with a corresponding lumen of the multi-lumen tube when the manifold mates with the multi-lumen tube.

In another aspect, a medical fluid pumping system comprises a medical fluid pumping machine, a medical fluid cassette, and a multi-lumen tube. The medical fluid pumping machine comprises a cassette compartment. The medical fluid cassette is configured to be disposed in the cassette compartment of the medical fluid pumping machine. The medical fluid cassette is connected to a manifold comprising multiple connection ports. The multi-lumen tube comprises a first end, a second end, an outer wall extending between the first end and the second end, and multiple lumens disposed within the outer wall. The first end of the multi-lumen tube is configured to be connected to the manifold. Each of the lumens is configured to mate with a corresponding one of the fluid connection ports of the manifold when the first end of the multi-lumen tube is connected to the manifold.

In a further aspect, a multi-lumen tube is mated to a manifold of a medical fluid cassette. The multi-lumen tube comprises multiple lumens disposed within an outer wall of the multi-lumen tube. The manifold comprises multiple fluid connection ports. Mating the multi-lumen tube to the manifold comprises mating each of the lumens of the multi-lumen tube to a corresponding one of the fluid connection ports of the manifold. A medical fluid is flowed through each of the lumens of the multi-lumen tube to the medical fluid cassette.

Embodiments can include one or more of the following features.

In some embodiments, each fluid connection port of the manifold comprises a tapered boss configured to mate with the corresponding passage of the adapter.

In some embodiments, one of the passages defined by the adapter connects one of the fluid connection ports of the manifold to a volume interior to the outer wall of the multi-lumen tube but exterior to each of the lumens when the adapter is mated with the manifold and the multi-lumen tube.

In some embodiments, the threaded end of the manifold is female, and the threaded first end of the threaded connector is male.

In some embodiments, the assembly further includes a second manifold configured to mate with the multi-lumen tube opposite the first manifold.

In some embodiments, the second manifold is configured to be connected to multiple fluid lines to place each of the fluid lines in fluid communication with a corresponding one of the lumens of the multi-lumen tube.

In some embodiments, the assembly further includes fluid pouches connected to the fluid lines.

In some embodiments, at least one of the fluid pouches connected to the fluid lines contains a dialysis fluid.

In some embodiments, the assembly further includes a medical fluid cassette.

In some embodiments, the medical fluid cassette is a dialysis fluid cassette.

In some embodiments, the dialysis fluid cassette is a peritoneal dialysis fluid cassette.

In some embodiments, the manifold is coupled to the cassette.

In some embodiments, each passage connects one of the fluid connection ports of the manifold to a corresponding port of the medical fluid cassette.

In some embodiments, the manifold is permanently connected to the cassette.

In some embodiments, the manifold is integrally formed with the cassette.

In some embodiments, the multi-lumen tube includes three or more lumens.

In some embodiments, the manifold is permanently connected to the body of the medical fluid cassette.

In some embodiments, the manifold is integrally formed with the body of the medical fluid cassette.

In some embodiments, the medical fluid cassette further includes a film attached to the body, and the film and the body cooperate to define the fluid passages.

In some embodiments, the medical fluid pumping system further includes multiple fluid pouches fluidly connected to the second end of the multi-lumen tube.

In some embodiments, fluid is flowed through a volume interior to the outer wall of the multi-lumen tube but exterior to each of the lumens.

Embodiments can include one or more of the following advantages.

In some embodiments, the multi-lumen tube can be used instead of multiple separate tubes. This can make setting up the medical fluid pumping system (e.g., by connecting the various tubes to the medical fluid pumping machine) faster and easier. In cases in which the dialysis is being conducted at a clinic, the use of the multi-lumen tube assembly can reduce downtime in between treatments.

Because the multi-lumen tube assembly can reduce the number of separate tubes used in the medical fluid pumping system, use of the multi-lumen tube can also reduce the risk of tubes becoming tangled during set up or treatment.

Because the multi-lumen tube assembly can reduce the number of connections required by a user, use of the multi-lumen tube can also reduce the risk of misconnections, such as connecting a fluid source pouch to an incorrect fluid port. The use of the multi-lumen tube can also reduce the risk of contamination, which is increased with each occurrence of handling by a user.

In embodiments in which multiple, disparate fluids simultaneously flow through the multi-lumen tube, the multi-lumen tube assembly can allow heat to be transferred amongst the multiple fluids, while also preventing mass transfer amongst the multiple fluids. For example, heat can be transferred from spent dialysate to fresh dialysate as both fluids flow through separate lumens of the multi-lumen tube.

The details of one or more embodiments of the subject matter of this disclosure are set forth in the accompanying drawings and the description. Other aspects, features, and advantages of the subject matter described herein will become apparent from the description, the drawings, and the claims.

DESCRIPTION OF DRAWINGS

FIG. 3A is an exploded perspective view of certain components of the multi-lumen tube assembly shown in FIG. 2.

FIG. 3B is a view of an adapter of the multi-lumen tube assembly shown in FIG. 2.

FIG. 6A is a view of another PD system including a PD cycler and a medical fluid cassette that is connected to multiple fluid pouches via a multi-lumen tube assembly.

DETAILED DESCRIPTION

A dialysis system (e.g., a peritoneal dialysis (PD) system or a hemodialysis (HD) system) can include a multi-lumen tube assembly that is configured to simultaneously connect multiple sources of fluid (e.g., multiple fluid pouches) to a single component (e.g., a dialysis fluid cassette) of the dialysis system.

Figure 1:
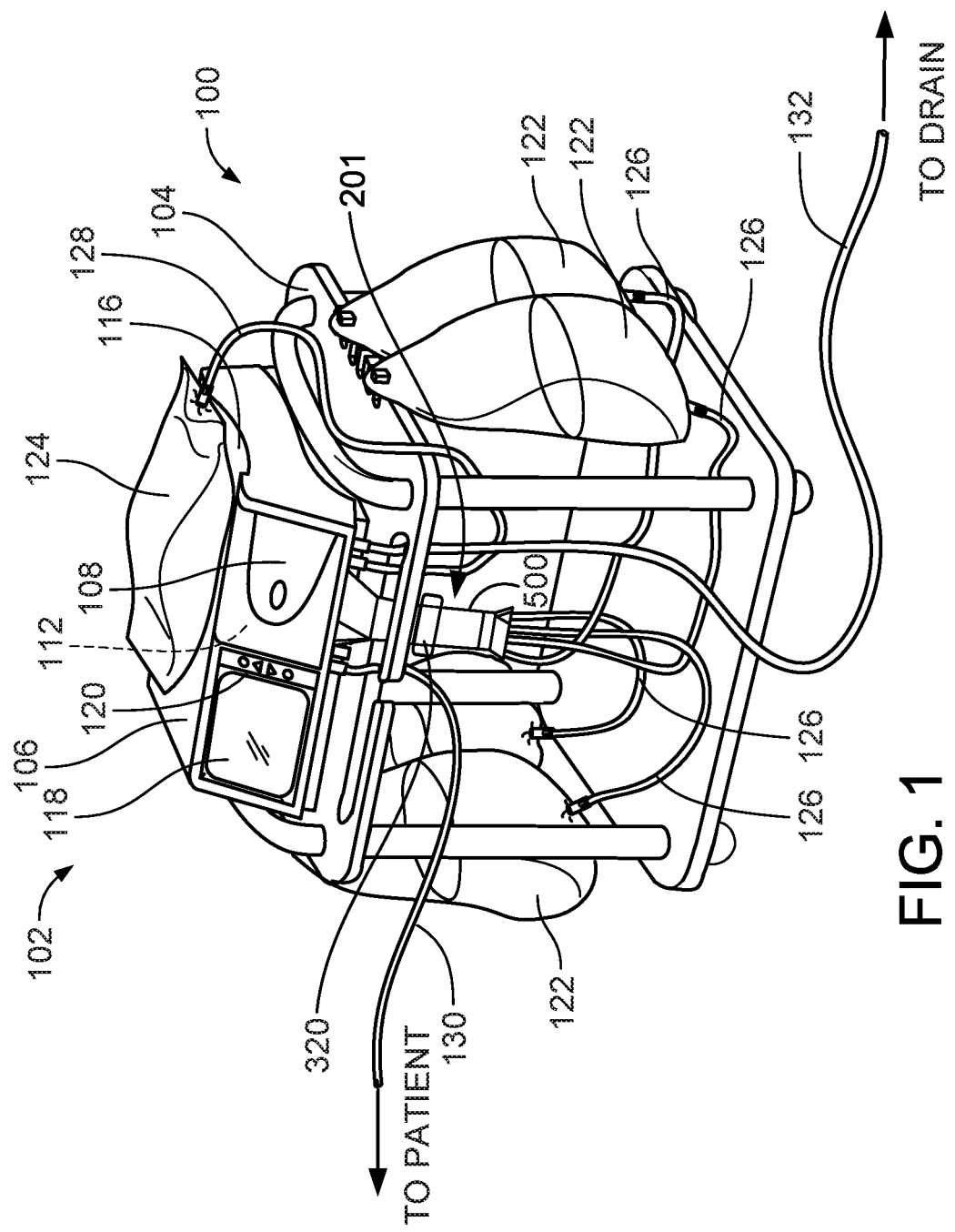
FIG. 1 is a perspective view of a peritoneal dialysis (PD) system.

Referring to FIG. 1, a PD system 100 includes a PD cycler 102 (also referred to as a PD machine) seated on a cart 104. The PD cycler 102 includes a housing 106 and a door 108 (shown as closed in FIG. 1). A PD cassette 112 (hidden from view behind the closed door 108) can be disposed within the housing 106 and interface with the PD cycler 102. The PD cycler 102 includes piston pumps that are operable to draw fresh dialysate into pump chambers of the PD cassette 112 from dialysate pouches 122 and then to pump that fresh dialysate to a patient connected to the PD system 100. The piston pumps can then be operated to draw spent dialysate from the patient into the pump chambers of the PD cassette 112 and then to pump the spent dialysate to a drain. Reciprocation of pistons of the piston pumps causes fluid to be alternately drawn into and forced out of the fluid pump chambers in the PD cassette 112. This process of drawing fluid into the fluid pump chambers and then forcing the fluid out of the fluid pump chambers can be repeated until a desired volume of the fluid has been pumped to or from a desired source (e.g., to or from the dialysate pouches 122, to or from the patient, etc.).

A heater tray 116 is positioned on top of the housing 106. The heater tray 116 is sized and shaped to accommodate a heater pouch 124 (e.g., a 5-liter heater pouch). The PD cycler 102 also includes a touch screen 118 and additional control buttons 120 that can be operated by the user to allow, for example, set-up, initiation, and/or termination of a PD treatment.

Dialysate pouches 122 are suspended on the sides of the cart 104, and a heater pouch 124 is positioned in the heater tray 116. The dialysate pouches 122 are connected to the cassette 112 via fluid lines 126 connected to a multi-lumen tube assembly 201 (shown also in FIG. 2). As an example, the fluid lines 126 and the multi-lumen tube assembly 201 can be used to pass dialysate from dialysate pouches 122 to the cassette 112 during use. The heater pouch 124 is connected to the cassette 112 via the heater pouch line 128. Dialysate can pass back and forth between the cassette 112 and the heater pouch 124 via the heater pouch line 128 during use. In addition, a patient line 130 and a drain line 132 are connected to the cassette 112. The patient line 130 can be connected to a patient's abdomen via a catheter and can be used to pass fluid back and forth between the cassette 112 and the patient's peritoneal cavity during use. The drain line 132 can be connected to a drain or drain receptacle and can be used to pass spent dialysate (e.g., dialysate withdrawn from the patient's peritoneal cavity through the patient line 130) from the cassette 112 to the drain or drain receptacle during use.

Figure 2:
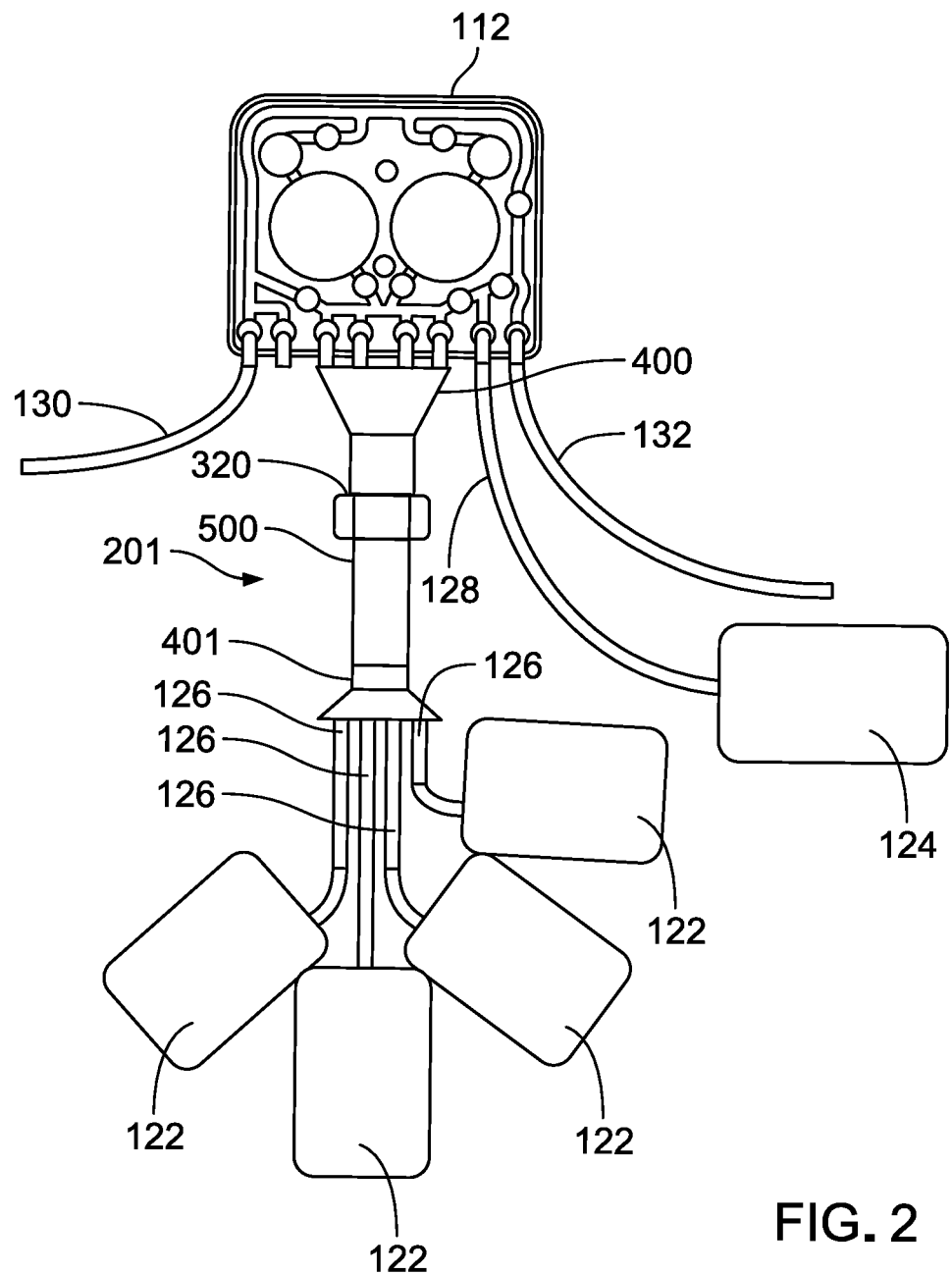
FIG. 2 is a view of a medical fluid cassette of the PD system shown FIG. 1 connected to multiple fluid pouches via a multi-lumen tube assembly.
Figure 4B:
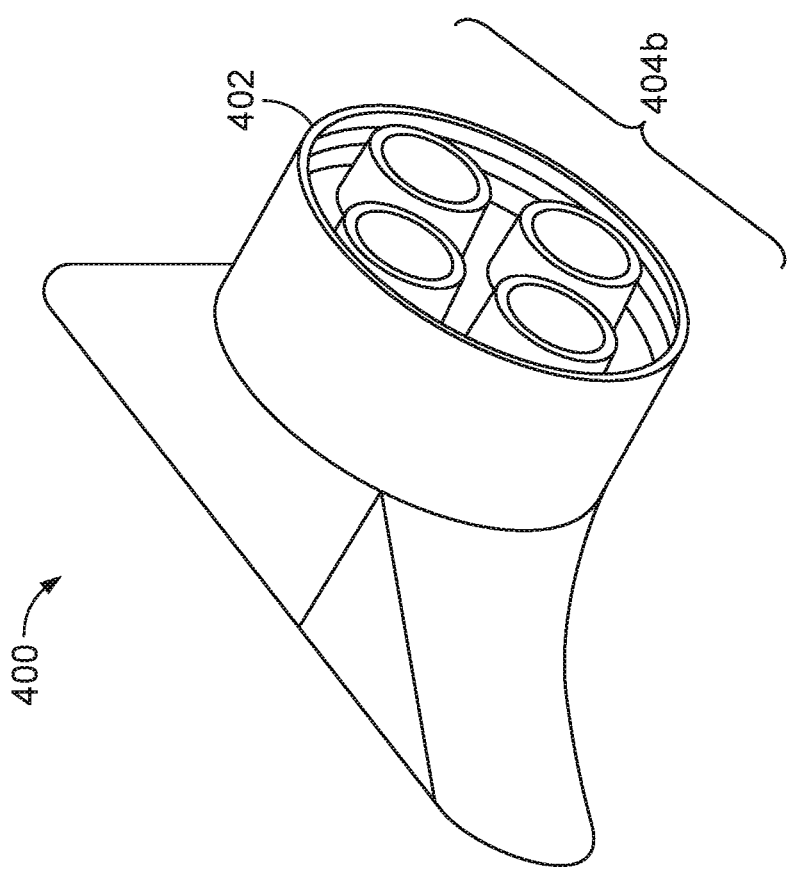
FIG. 4B is a view of an opposite end of the manifold shown in FIG. 4A.
Figure 4A:
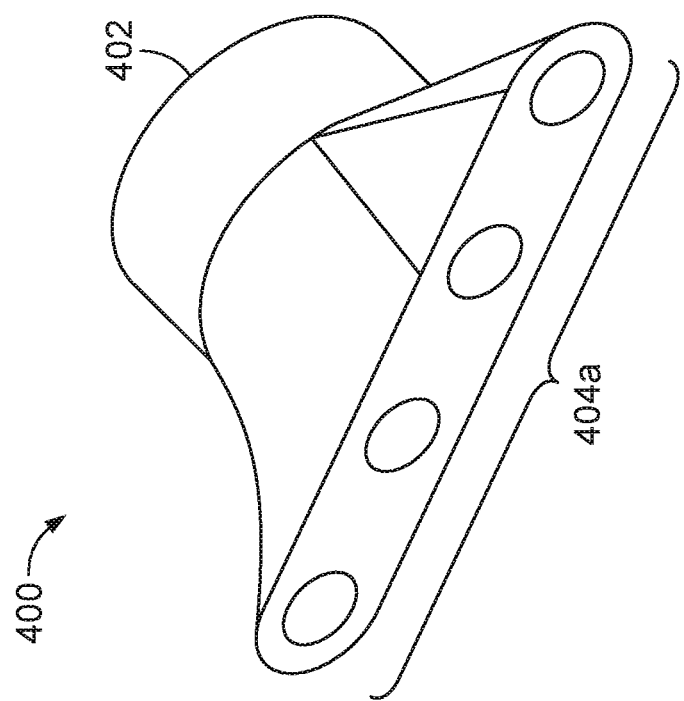
FIG. 4A is a view of one end of a manifold of the multi-lumen tube assembly shown in FIG. 2.

Referring to FIGS. 2, 4A, and 4B, the cassette 112 is connected to a first manifold 400 of the multi-lumen tube assembly 201. More specifically, fluid connection ports 404a at a first end of the first manifold 400 are connected to fluid ports extending from the bottom of the cassette 112. In some implementations, the first manifold 400 is permanently connected to the cassette 112. For example, the fluid connection ports 404a can be laser welded, thermally bonded, ultrasonically bonded, or adhesively bonded to the fluid ports of the cassette 112. The first manifold 400 permits fluid to flow from multiple lumens within the multi-lumen tube 500 into the cassette 112.

The multi-lumen tube assembly 201 also includes a second manifold 401 connected to the multi-lumen tube 500. The first manifold 400 and the second manifold 401 are connected to opposite ends of the multi-lumen tube 500. While the first manifold 400 connects the cassette 112 to the multi-lumen tube 500, the second manifold 401 connects the multi-lumen tube 500 to the dialysate pouches 122 via the fluid lines 126. The fluid lines 126 can be connected to the second manifold 401 in any of the various ways described herein for connecting the first manifold 400 to the cassette 112. Dialysate can pass from one or more of the dialysate pouches 122 to the cassette 112 (or vice versa) through the manifolds 400 and 401 and the multi-lumen tube 500. The multi-lumen tube assembly 201 permits the user to make a single connection at the cassette 112 to provide fluid communication between each of the dialysate pouches 122 and the cassette 112, as opposed to having to make four separate connections at the cassette 112.

FIG. 3A shows an exploded view of the multi-lumen tube assembly 201. The multi-lumen tube 500 is connected to the first manifold 400 via an adapter 310. The adapter 310 includes a first end 312 and a second end 314 opposite the first end 312. The adapter 310 defines passages between the first end 312 and the second end 314. When the first end 312 of the adapter 310 is connected to the threaded second end 402 of the first manifold 400, each passage of the adapter 310 is connected to a different fluid connection port 404b of the first manifold 400. When the second end 314 of the adapter 310 is connected to the multi-lumen tube 500, each passage of the adapter 310 is connected to a different individual lumen 504 of the multi-lumen tube 500. Therefore, when the adapter 310 is connected to both the first manifold 400 and the multi-lumen tube 500, each passage of the adapter 310 connects one of the fluid connection ports 404b of the first manifold 400 to a different one of the individual lumens 504 of the multi-lumen tube 500.

Each of the fluid connection ports 404b of the first manifold 400 includes a tapered boss that allows the fluid connection port 404b to plug into the respective passage of the adapter 310. The tapered bosses of the fluid connection ports 404b are sized and shaped to connect to the passages defined in the adapter 310 in a fluid-tight manner (e.g., via friction fit).

FIG. 3B shows another view of the adapter 310. The adapter 310 includes four tubular members 316 that can fit into the lumens 504 of the multi-lumen tube 500.

Referring back to FIG. 3A, the adapter 310 connected to the first manifold 400 and the multi-lumen tube 500 can be secured in position by a threaded connector 320. The threaded connector 320 includes a first end 322 and a second end 324 opposite the first end 322. The threaded connector 320 defines an inner bore between the first end 322 and the second end 324. The inner bore of the threaded connector 320 is configured to receive the adapter 310. The first end 312 of the adapter 310 has an outer diameter that is larger than the diameter of the inner bore of the threaded connector 320. The remainder of the adapter 310 has an outer diameter that is equal to or smaller than the diameter of the inner bore of the threaded connector 320. The threaded connector 320 can therefore receive within its inner bore the second end 314 of the adapter 310, all the way up to but not including the first end 312 of the adapter 310 (due to the larger outer diameter of the first end 312). This can prevent the adapter 310 and the multi-lumen tube 500 from becoming detached from the threaded connector 320 during use. The threaded connector 320 is rotatable relative to the adapter 310. For example, while the adapter 310 is received by the inner bore of the threaded connector 320, the threaded connector 320 can rotate relative to the adapter 310. This allows the threaded connector 320 to be rotated to secure the threaded connector, the adapter 310, and the multi-lumen tube 500 to the first manifold 400 without rotating the adapter 310 and the multi-lumen tube 500, which would cause those components to become misaligned with the first manifold 400.

The first end 322 of the threaded connector 320 is threaded and configured to mate with the threaded second end 402 of the first manifold 400. In the implementation shown in FIG. 3A, the threaded first end 322 of the threaded connector 320 is male, and the threaded second end 402 of the first manifold 400 is female. Mating the threaded first end 322 of the threaded connector 320 to the threaded second end 402 of the first manifold 400 while the adapter 310 is received by the inner bore of the threaded connector 320 can secure the connection of the adapter 310 to the first manifold 400 in a fluid-tight manner. The threaded connector 320 includes tabs 326a and 326b that can be grasped by the user to more easily rotate the threaded connector 320 and mate the threaded ends 402 and 322 together.

The multi-lumen tube 500 can be secured to the adapter 310 using any of various suitable techniques, including but not limited to friction fit, adhesive bond, thermal bond, etc.

Figure 5:
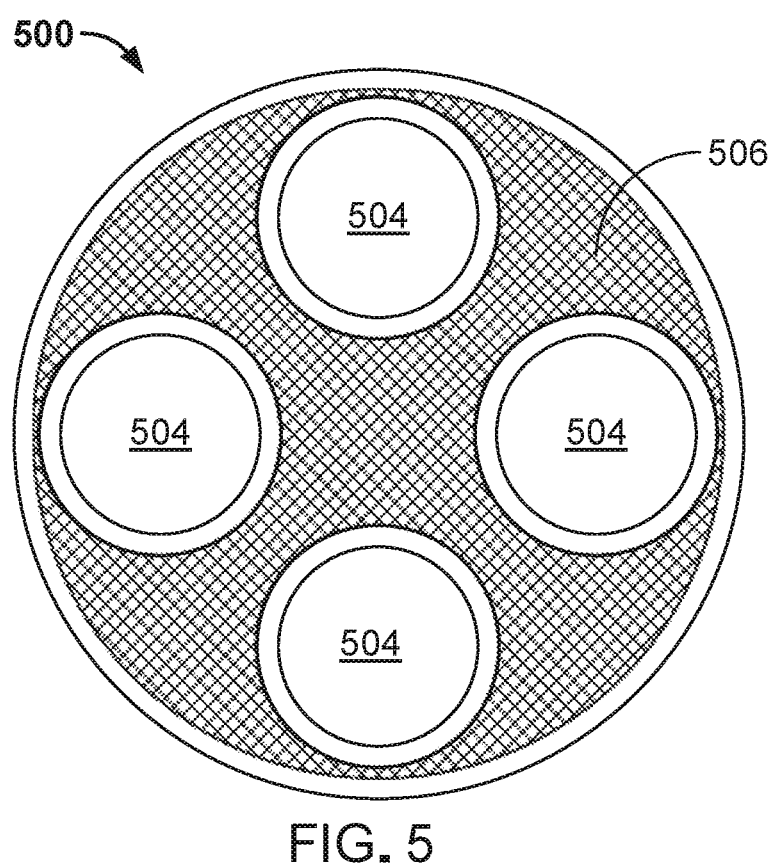
FIG. 5 is a cross-sectional view of a multi-lumen tube of the multi-lumen tube assembly shown in FIG. 2.

FIGS. 4A and 4B are enlarged perspective views showing different ends of the first manifold 400. The first manifold 400 includes the fluid connection ports 404a at the first end for connection to the cassette 112. The second end 402 of the first manifold 400 is threaded, and the first manifold 400 includes the fluid connection ports 404b at the threaded second end 402. Each fluid connection port 404a at the first end is connected to a different one of the fluid connection ports 404b at the second threaded end 402. Referring also to FIG. 5, the multiple lumens 504 of the multi-lumen tube 500 extend within an outer wall of the multi-lumen tube 500. The fluid connection ports 404b are sized and shaped to connect to the lumens 504 of the multi-lumen tube 500 via the adapter 310 in a fluid-tight manner (e.g., via friction fit). Each fluid connection port 404b at the threaded second end 402 can be connected to a different one of the lumens 504 of the multi-lumen tube 500. The lumens 504 can allow various fluid streams to flow through the multi-lumen tube 500 without interacting with each other (e.g., without mixing) within the multi-lumen tube 500. The volume 506 is defined as the volume within the outer wall of the multi-lumen tube 500 and exterior to the lumens 504.

The second manifold 401 will not be described in detail. It should be understood that the second manifold 401 can have a similar construction to the first manifold 400 (shown in FIGS. 4A and 4B) and can be connected to the multi-lumen tube 500 and the fluid lines 126 in much the same way that the first manifold 400 is connected to the multi-lumen tube 500 and the fluid ports of the cassette 112.

The adapter 310 can be made of a material that is suitable for bonding to the multi-lumen tube 500. For example, the adapter 310 can be made of acrylonitrile butadiene styrene (ABS), polycarbonate (PC) plastic, poly(methyl methacrylate) (PMMA), or high impact polystyrene (HIPS). The manifolds 400 and 401 can also be made of a material that is suitable for bonding to the multi-lumen tube 500. For example, the manifolds 400 and 401 can be made of ABS, PC, PMMA, or HIPS. Any of various other medical grade materials can alternatively be used to form the adapter 310, the threaded connector 320, and the manifolds 400, 401. An example of such materials include polyvinyl chloride (PVC).

The multi-lumen tube 500 is typically made of one or more polymers, such as silicone rubber, nylon, polyurethane, polyethylene terephthalate (PET), latex, and thermoplastic elastomers. However, other suitable medical grade tubing materials may be used.

Referring back to FIGS. 1 and 2, to set up the PD system 100 for treatment, the user typically first connects the multi-lumen tube 500 to the cassette 112 by screwing the adapter 320 into the threaded end of the first manifold 400, which is pre-connected to the cassette 112. The multi-lumen tube 500 is similarly connected to the manifold 401, which is pre-connected to the fluid lines 126, by screwing the adapter at the opposite end of the multi-lumen tube 500 into a threaded end of the second manifold 401. This allows the four fluid lines 126 to be fluidly connected to the cassette 112 in two easy steps. Setting up many prior systems required the user to individually connect each of the fluid lines to the cassette, which was more time consuming and cumbersome. The multi-lumen tube assembly 201 described herein reduces the time required to set up the PD system 100 for treatment and reduces the risk of the fluid lines 126 becoming entangled.

After connecting the multi-lumen tube 500 to the cassette 112 and the fluid lines 126, the cassette 112 is connected to the face of the PD cycler 102 and the door 108 is closed to secure the cassette 112 between the door 108 and the face of the machine. The fluid lines 126 are then connected to the dialysate pouches 122. The patient and drain lines 130, 132 are also connected to the patient and a drain, respectively. The PD system is then ready for treatment.

The PD treatment typically begins by emptying the patient of spent dialysate that remains in the patient's abdomen from the previous treatment. To do this, the pump of the PD cycler 102 is activated to cause the spent dialysate to be drawn into the fluid pump chamber of the cassette 112 from the patient. The spent dialysate is then pumped from the fluid pump chamber to the drain via the drain line 132.

After draining the spent dialysate from the patient, heated fresh dialysate is transferred to the patient. For example, fresh dialysate can be transferred from one of the dialysate pouches 122 to the heater pouch 124 and then from the heater pouch 124 to the patient's peritoneal cavity. To do this, the pump of the PD cycler 102 is activated to cause fresh dialysate to be drawn into the fluid pump chamber of the cassette 112 from one of the dialysate pouches 122 via the corresponding fluid line 126. The fresh dialysate is then pumped from the fluid pump chamber of the cassette 112 to the heater pouch 124 via the heater pouch line 128. The heater tray 116 then heats the fresh dialysate in the heater pouch 124. Once the fresh dialysate is heated, the pump of the PD cycler 102 is activated to cause the heated fresh dialysate to be drawn into the fluid pump chamber of the cassette 112 from the heater pouch 124 via the heater pouch line 128. The heated fresh dialysate is then pumped from the fluid pump chamber of the cassette 112 to the patient via the patient line 130.

Once the heated fresh dialysate has been pumped from the heater bag 124 to the patient, the dialysate is allowed to dwell within the patient for a period of time. During this dwell period, toxins cross the peritoneum of the patient in to the dialysate from the patient's blood. As the dialysate dwells within the patient, the PD cycler 102 can prepare fresh dialysate (for example, from another one of the dialysate pouches 122) for delivery to the patient in a subsequent cycle. These steps can be repeated with the dialysate from the remaining dialysate pouches 122. The dialysate from the last of the dialysate pouches 122 is typically delivered to the patient and left in the patient until the subsequent PD treatment.

While the dialysate has been described as being pumped into the heater pouch 124 from one of the dialysate pouches 122 at a time, dialysate can alternatively be simultaneously pumped into the heater pouch 124 from multiple different dialysate pouches 122. Such a technique may be advantageous, for example, where the dialysate in the pouches 122 has different concentrations (e.g., different dextrose concentrations) and a desired concentration for treatment is intermediate to the concentrations of the dialysate in two or more of the pouches 122.

While the cassette 112 and the first manifold 400 have been described and illustrated as being formed as separate components that are subsequently fixed together, in some embodiments, the cassette 112 and the first manifold 400 are formed integrally as a unitary body (e.g., the cassette 112 includes the first manifold 400).

While the components of the PD system 100 have been described and illustrated as having certain dimensions, shapes, and profiles, in some embodiments, a PD system that is otherwise substantially similar in construction and function to the PD system 100 may include one or more components that have one or more dimensions, shapes, and/or profiles that are different from those described above with respect to the PD system 100. For example, the first manifold 400, the second manifold 401, the multi-lumen tube 500, the adapter 310, and the threaded connector 320 can each have a different dimension, shape, and/or profile from the respective ones shown in the figures, as long as the various components can match up together to form a PD system that is otherwise similar in construction and function to the PD system 100. As a non-limiting example, the first threaded end 322 of the threaded connector 320 can be female, and the second threaded end 402 of the first manifold 400 can be male.

While the first manifold 400 has been described as being permanently connected to or integrally formed with the cassette 112, in some implementations, the first manifold is releasably connected to the cassette 112. In such implementations, for example, the fluid connection ports 404a of the first manifold are connected to the fluid ports of the cassette 112 using a friction fit.

As another non-limiting example, the first manifold 400 can include more than four fluid connection ports 404a and more than four fluid connection ports 404b. In some embodiments, for example, the first manifold 400 includes five fluid connection ports 404a and five fluid connection ports 404b, and the multi-lumen tube 500 includes five lumens 504. In such embodiments, five dialysate pouches 122 can be connected to the cassette 112 via the multi-lumen tube assembly 201. Alternatively, four dialysate pouches 122 and the heater pouch 124 can be connected to the cassette 112 via the multi-lumen tube assembly 201. In such an embodiment, the only lines connected to the cassette 112 could be the multi-lumen tube assembly 201, the patient line 130, and the drain line 132. Alternatively, three dialysate pouches 122, the heater pouch 124, and the drain line 132 can be connected to the cassette 112 via the multi-lumen tube assembly 201. In such an embodiment, the only lines connected to the cassette 112 could be the multi-lumen tube assembly 201 and the patient line 130.

In some embodiments, the manifold 400 includes fewer than four (e.g., two or three) connection ports 404a and fewer than four (e.g., two or three) fluid connection ports 404b.

As another non-limiting example, although shown in FIG. 2 as including two manifolds 400 and 401, in some embodiments, only the first manifold 400 may be used (to connect the cassette 112 to the multi-lumen tube 500) because the lumens 504 of the multi-lumen tube 500 can be connected to the dialysate pouches 122 (via the fluid lines 126) without the use of the second manifold 401. Although shown in FIG. 2 as being different in size, the two manifolds 400 and 401 can be similar in size and in construction. Similarly, the second manifold 401 can include the same features as the first manifold 400. For example, the second manifold 401 has fluid connection ports on opposite ends of the second manifold 401 (similar to the fluid connection ports 404a and 404b on opposite ends of the first manifold 400).

Although described and illustrated as being solid, the volume 506 of the multi-lumen tube 500 can be void space. For example, in some embodiments, the cross-hatched area of volume 506 in FIG. 5, can be void space through which a fluid can flow. For example, a heated fluid can be flowed in the volume 506, such that heat can be transferred to a fluid flowing in one of the lumens 504. In this way, one of more fluids flowing through the multi-lumen tube 500 can be pre-heated before entering the cassette 112 and subsequently the patient.

In some embodiments, fluid from the user can be transferred to one of the dialysate pouches 122. In some embodiments, fluid from the user can be transferred to two or more dialysate pouches 122 simultaneously. In some embodiments, fluid from one of the dialysate pouches 122 can be transferred to the user while fluid from the user is being transferred to another of the dialysate pouches 122. Flowing multiple fluid streams through the passages defined in the multi-lumen tube 500 (e.g., the lumens 504 and/or the volume 506) simultaneously can allow for heat transfer across the fluid streams, while preventing mass transfer across the fluid streams.

As described above, in addition to being used to connect the dialysate pouches 122 to the cassette 112, in some embodiments, the multi-lumen tube assembly 201 is used to connect other pouches, such as the heater pouch 124, to the cassette 112. In embodiments in which the heater pouch 124 is connected to the multi-lumen tube assembly and the volume 506 (shown in FIG. 5) of the multi-lumen tube 500 is void space, the heater pouch 124 can be connected to the volume 506 to provide heating to the fluid flowing in one or more of the lumens 504.

While the PD system 100 has been described and illustrated as including piston pumps, in some embodiments, a PD system that is otherwise similar in construction and function to the PD system 100 may include one or more peristaltic pumps instead of piston pumps. FIG. 6A, for example, illustrates another PD system 600 including a cycler 51 and a cassette 112' including a pumping element 61 (e.g., a liquid distribution system) that, when connected to the cycler 51, forms a peristaltic pump. The cassette 112' can be inserted into a slot 50 of the cycler 51 and then lowered. Alternatively, the cassette 112' can be inserted into the slot 50 and then a platform beneath the cassette 112' can be raised to engage the cassette 112'. As the cassette 112' is lowered within the slot 50 or the underlying platform is raised, a central opening in the pumping element 61 receives a shaft of the cycler 51 to form the peristaltic pump. The pumping element 61 can then be motor driven by the shaft of the cycler 51, resulting in peristaltic movement of fluid through the cassette 112'.

Unlike the PD system 100 described above, the PD system 600 is equipped with an in-line heater. The heater is disposed within the cycler 51 and located adjacent a heating portion of the cassette 112' when the cassette 112' is positioned in the slot 50 of the cycler 51. As dialysate is pumped through the cassette 112', the dialysate is heated by the heater. Thus, the PD system 600 need not include a separate warming bag in which the dialysate is heated.

Much like the cassette 112 described above, the cassette 112' of the PD system 600 includes four ports that are connected to the fresh dialysate pouches 122 via the multi-lumen tube assembly 201. The cassette 112' also includes a port connected to a patient line and a port connected to a drain line. The PD system 600 can be set up and operated in much the same way as the PD system 100 discussed above. The multi-lumen tube assembly 201 can simplify the set up and reduce the risk of lines extending from the cassette 112' becoming entangled during set up and treatment.

Figure 6B:
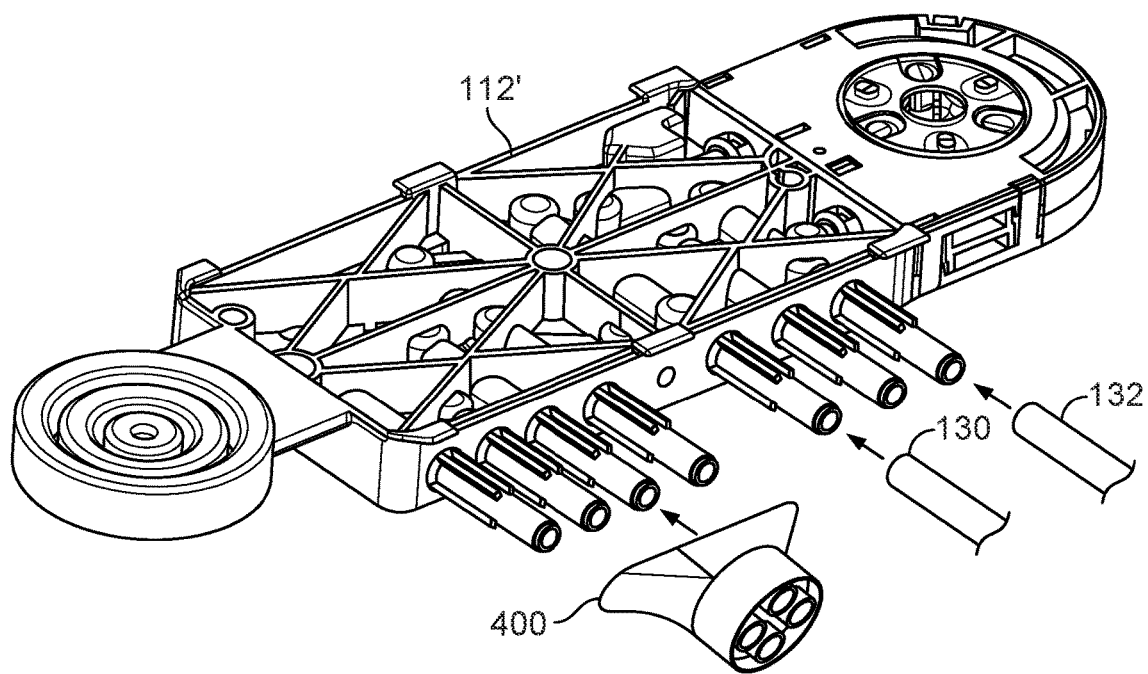
FIG. 6B is another view of the medical fluid cassette shown in FIG. 6A.

FIG. 6B shows another view of the cassette 112'. Four of the ports can connect to the first manifold 400 of the multi-lumen tube assembly 201. One of the ports can connect to the patient line 130, and another one of the ports can connect to the drain line 132.

Figure 6C:
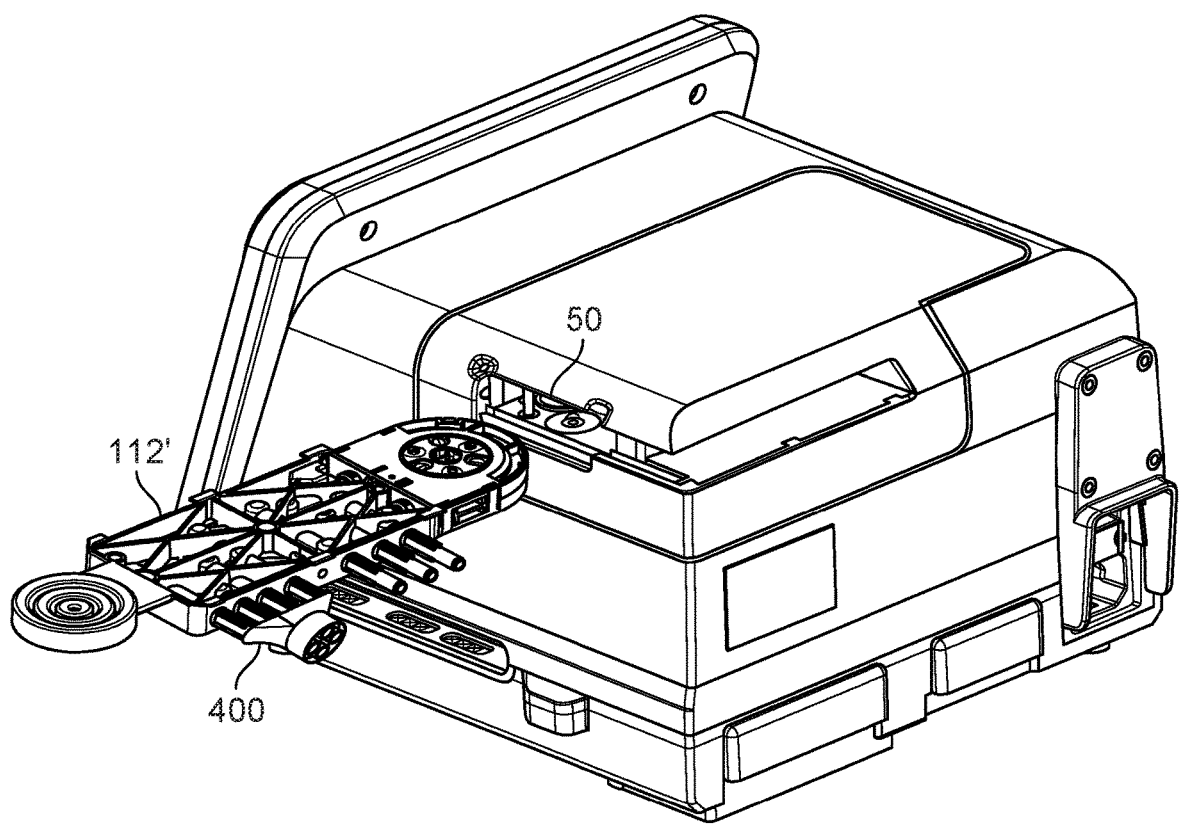
FIG. 6C is another view of the PD system of FIG. 6A, showing the medical fluid cassette being loaded into the PD cycler.
Figure 6D:
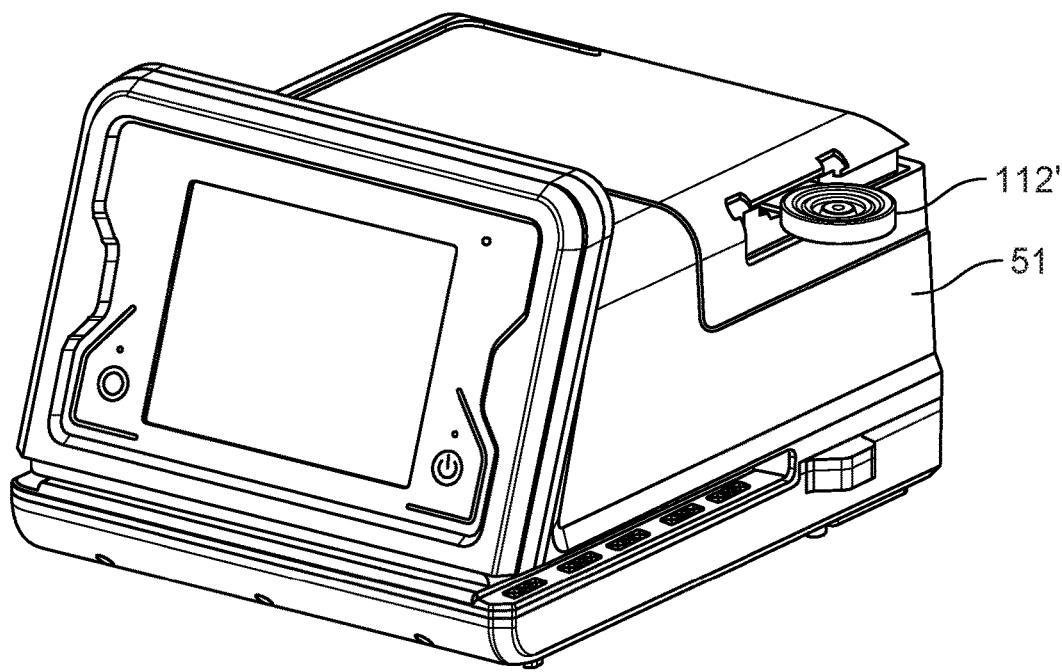
FIG. 6D is a front perspective view of the PD system of FIG. 6A with the medical fluid cassette loaded in the PD cycler.
Figure 6E:
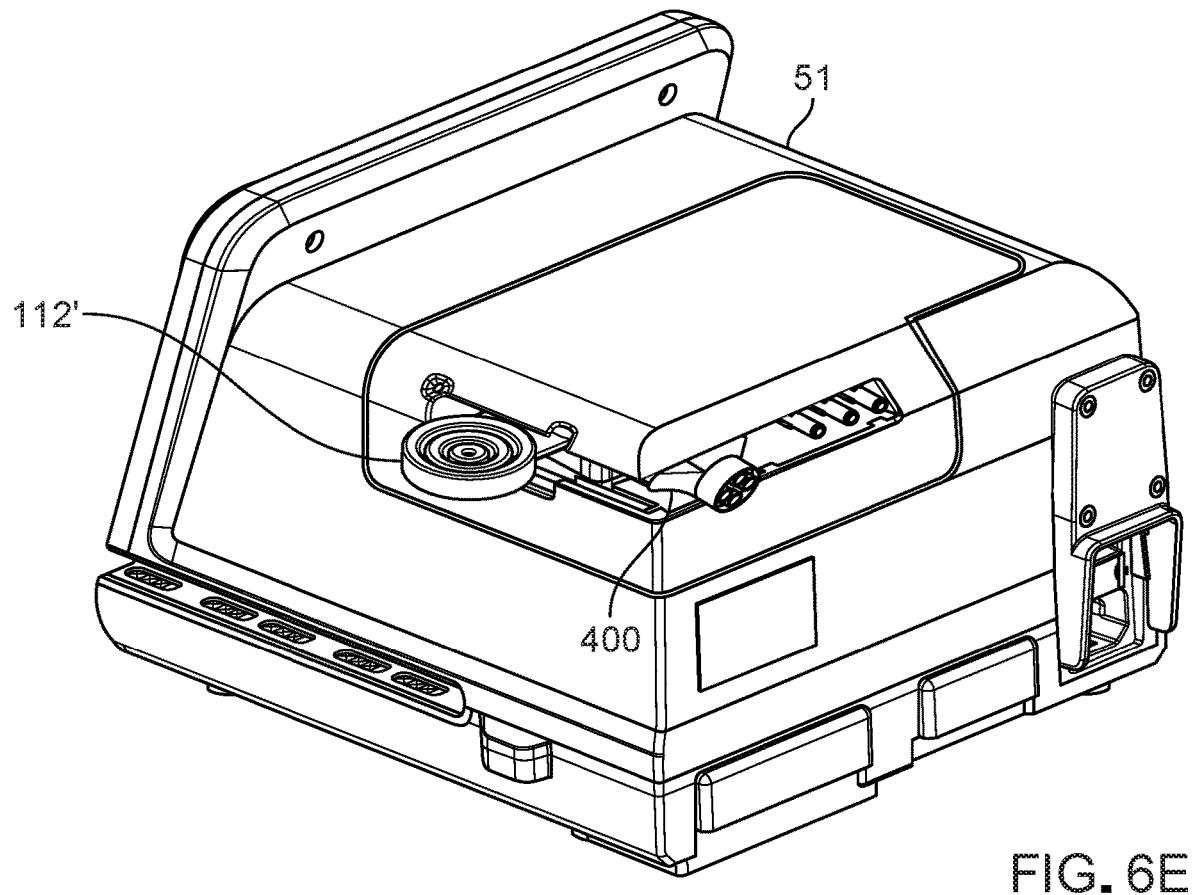
FIG. 6E is a rear perspective view of the PD system of FIG. 6A with the medical fluid cassette loaded in the PD cycler.

FIG. 6C shows another view of the cassette 112' and the cycler 51. As described previously, the cassette 112' can be inserted into the slot 50 of the cycler 51. FIG. 6D shows a front perspective view of the cassette 112' inserted into the cycler 51, and FIG. 6E shows a rear perspective view of the cassette 112' inserted into the cycler 51.

While the cassette 112 has been described and illustrated as being included and/or used in the PD system 100, in some embodiments, a medical fluid cassette that is otherwise similar in construction and/or function to the PD cassette may be used in other types of medical fluid pumping systems. For example, the cassette 112 can be used in a hemodialysis (HD) system, a hemofiltration (HF) system, and a hemodiafiltration (HDF) system. In such cases, the cassette 112 can be used to pump or carry dialysate and/or blood. In some cases, the multi-lumen tube assembly 201 connected to the cassette 112 carries both blood and dialysate to/from the cassette 112.

Other embodiments are within the scope of the following claims.

What is claimed is:

1. An assembly comprising:
a first manifold comprising a threaded portion and a plurality of fluid connection ports, the first manifold configured to couple to a medical fluid cassette;
a multi-lumen tube comprising a plurality of lumens within an outer wall of the multi-lumen tube, the multi-lumen tube having a first end and a second end opposite the first end;
an adapter comprising a first end and a second end opposite the first end, wherein:
the first end of the adapter is configured to mate with the manifold;
the second end of the adapter is configured to mate with the first end of the multi-lumen tube;
the adapter defines a plurality of passages between the first and second ends of the adapter; and
each passage connects one of the fluid connection ports of the manifold to a corresponding lumen of the multi-lumen tube when the adapter is mated with the manifold and the multi-lumen tube;
a threaded connector comprising a first end and a second end opposite the first end, the threaded connector defining an inner bore between the first and second ends of the threaded connector, the inner bore of the threaded connector configured to receive the adapter, the threaded connector being rotatable relative to the adapter, and the first end of the threaded connector being threaded and configured to mate with the threaded portion of the manifold to secure the adapter to the manifold;
a second manifold configured to mate with the second end of the multi-lumen tube;
a plurality of fluid lines configured to be connected to the second manifold such that each of the fluid lines is in fluid communication with a corresponding one of the lumens of the multi-lumen tube; and
a plurality of fluid bags configured to be connected to the plurality of fluid lines.

2. The assembly of claim 1, wherein each fluid connection port of the manifold comprises a tapered boss configured to mate with the corresponding passage of the adapter.

3. The assembly of claim 1, wherein one of the passages defined by the adapter connects one of the fluid connection ports of the manifold to a volume interior to the outer wall of the multi-lumen tube but exterior to each of the lumens when the adapter is mated with the manifold and the multi-lumen tube.

4. The assembly of claim 1, wherein the threaded end of the manifold is female, and the threaded first end of the threaded connector is male.

5. The assembly of claim 1, wherein at least one of the fluid pouches connected to the fluid lines contains a dialysis fluid.

6. The assembly of claim 1, further comprising the medical fluid cassette.

7. The assembly of claim 6, wherein the medical fluid cassette is a dialysis fluid cassette.

8. The assembly of claim 7, wherein the dialysis fluid cassette is a peritoneal dialysis fluid cassette.

9. The assembly of claim 1, wherein the manifold is coupled to the cassette.

10. The assembly of claim 9, wherein each passage connects one of the fluid connection ports of the manifold to a corresponding port of the medical fluid cassette.

11. The assembly of claim 9, wherein the manifold is permanently connected to the cassette.

12. The assembly of claim 11, wherein the manifold is integrally formed with the cassette.

13. The assembly of claim 1, wherein the multi-lumen tube comprises three or more lumens.

14. A medical fluid cassette assembly comprising:
a body at least partially defining a plurality of fluid passages, the body comprising a plurality of fluid line connectors in fluid communication with the fluid passages;
a first manifold connected to the body, the first manifold comprising a plurality of fluid connection ports, the first manifold configured to mate with a first end of a multi-lumen tube comprising a plurality of lumens disposed within an outer wall of the multi-lumen tube, wherein each fluid connection port mates with a corresponding lumen of the multi-lumen tube when the first manifold mates with the first end of the multi-lumen tube;
a second manifold configured to mate with a second end of the multi-lumen tube;
a plurality of fluid lines configured to be connected to the second manifold such that each of the fluid lines is in fluid communication with a corresponding one of the lumens of the multi-lumen tube when the multi-lumen tube mates with the second end of the second manifold; and
a plurality of fluid bags configured to be connected to the plurality of fluid lines.

15. The medical fluid cassette assembly of claim 14, wherein the manifold is permanently connected to the body of the medical fluid cassette.

16. The medical fluid cassette assembly of claim 14, wherein the manifold is integrally formed with the body of the medical fluid cassette.

17. The medical fluid cassette assembly of claim 14, further comprising a film attached to the body, the film and the body cooperating to define the plurality of fluid passages.

18. A medical fluid pumping system comprising:
a medical fluid pumping machine comprising a cassette compartment;
a medical fluid cassette configured to be disposed in the cassette compartment of the medical fluid pumping machine, the medical fluid cassette connected to a first manifold comprising a plurality of fluid connection ports; and
a multi-lumen tube comprising:
a first end;
a second end;
an outer wall extending between the first end and the second end;
a plurality of lumens disposed within the outer wall, wherein the first end of the multi-lumen tube is configured to be connected to the first manifold, and each of the lumens is configured to mate with a corresponding one of the fluid connection ports of the first manifold when the first end of the multi-lumen tube is connected to the first manifold;
a second manifold configured to mate with a second end of the multi-lumen tube;
a plurality of fluid lines configured to be connected to the second manifold such that each of the fluid lines is in fluid communication with a corresponding one of the lumens of the multi-lumen tube when the multi-lumen tube mates with the second end of the second manifold; and
a plurality of fluid bags configured to be connected to the plurality of fluid lines.

19. A method comprising:
mating a first end of a multi-lumen tube to a first manifold of a medical fluid cassette, wherein the multi-lumen tube comprises a plurality of lumens disposed within an outer wall of the multi-lumen tube, the first manifold comprises a plurality of fluid connection ports, and mating the first end of the multi-lumen tube to the first manifold comprises mating each of the lumens of the multi-lumen tube to a corresponding one of the fluid connection ports of the first manifold;

mating a second manifold to a second end of the multi-lumen tube;

mating a plurality of fluid lines to the second manifold such that each of the fluid lines is in fluid communication with a corresponding one of the lumens of the multi-lumen tube;

mating a plurality of fluid bags to the plurality of fluid lines; and flowing a medical fluid from each of the fluid bags through each of the lumens of the multi-lumen tube to the medical fluid cassette.

20. The method of claim 19, further comprising flowing fluid through a volume interior to the outer wall of the multi-lumen tube but exterior to each of the lumens.

* * * * *